United States Patent [19]
Roelofs

[11] Patent Number: 5,588,963
[45] Date of Patent: Dec. 31, 1996

[54] METHOD FOR LIQUID FLOW MEASURING AND APPARATUS TO PRACTICE THIS METHOD

[76] Inventor: Bernardus J. G. M. Roelofs, Dammestraat 1, NL 5628 NM Eindhoven, Netherlands

[21] Appl. No.: 240,665

[22] PCT Filed: Oct. 28, 1992

[86] PCT No.: PCT/NL92/00193
§ 371 Date: Apr. 29, 1994
§ 102(e) Date: Apr. 29, 1994

[87] PCT Pub. No.: WO93/09407
PCT Pub. Date: May 13, 1993

[30] Foreign Application Priority Data

Oct. 30, 1991 [NL] Netherlands ............................ 9101825

[51] Int. Cl.$^6$ .................................................... A61M 5/16
[52] U.S. Cl. .................................................... 604/65
[58] Field of Search .......................... 604/65–67, 30–34, 604/250–256, 49, 50, 246, 247; 128/DIG. 13, DIG. 12

[56] References Cited

U.S. PATENT DOCUMENTS 3,609,379  9/1971  Hildebrandt ............................ 250/218
4,328,801  5/1982  Marx et al. ............................ 128/214 E
4,680,977  7/1987  Coneno et al. ............................ 604/253
4,936,828  6/1990  Chiang .................................... 604/65
5,267,980  12/1993  Dirr, Jr. et al. ........................ 604/253
5,331,309  7/1994  Sakai ...................................... 604/31

FOREIGN PATENT DOCUMENTS 2458804  1/1981  France .
2207239  1/1989  United Kingdom .

OTHER PUBLICATIONS

Proceedings Computers in Cardiology, Publ. 1990, Los Alamitos, California, US pp. 405–406, R. Leor, E. A., "A system for the measurement of drop volume of introvenous solutions".

Primary Examiner—Manuel Mendez
Attorney, Agent, or Firm—David P. Gordon

[57] ABSTRACT

In a method to determine or regulate flows or flow rates of liquids such as those used in medical infusion systems, optical imaging means are used for real flow measuring. The increase in volume of drops hanging at an outlet and the increase of volume of liquid gathered in a container can be measured by image acquisition and image processing. This increase of volume represents a real time flow. As an example, signals obtained from these measurements can be used to control or adjust volume flow for medical treatment or medical diagnosis. An apparatus to carry out such a method can be composed of devices well known per se.

16 Claims, 2 Drawing Sheets

5,588,963

METHOD FOR LIQUID FLOW MEASURING AND APPARATUS TO PRACTICE THIS METHOD

BACKGROUND OF THE INVENTION

1. Field of the invention

The invention pertains to a method for measuring a liquid flow and flow rate using optical imaging means and to an apparatus to apply this method.

2. State of the Art

Methods and apparatus for measuring liquid flow rate are well known in the art. U.S. Pat. No. 4,936,828 discloses the use of a camera to measure the volume of falling drops in a liquid flow system and to count the total number of falling drops per unit of time in order to determine the flow rate of the liquid. Under this method, however, the smallest measurable change in the flow rate is limited to the volume of a completed falling drop.

Other known methods for liquid flow determination include measuring the liquid volume or mass per unit of time. Under these methods, the volume or mass of a liquid flowing out of a reservoir during a given period of time is measured to determine the flow over that period of time and the flow rate. The accuracy of such methods depends strongly on the time period over which the measured volume or mass of the liquid is divided, and on the precision of these measurements. These time integration techniques, however, prohibit the real time measurement of the flow in time and flow rate and are particularly unsuited for measuring small flow rates. Furthermore, existing flow measuring devices have a limited operating dynamic range, as it is difficult to combine in one piece of equipment, measurement means for both large and small flows.

Thus the major drawbacks associated with known methods and equipment for measuring the flow and flow rate include the facts that they are time consuming, inaccurate, sensitive to noise, evaporation, vibration, and viscosity, and most importantly, impracticable if real time measurements are desired. Known methods and equipment for measuring flow and flow rate are particularly unsuited for the measurement of especially small flows in medical infusion systems, where deviations from the stipulated flow of very small quantities can have disastrous medical consequences unless corrected or avoided.

SUMMARY OF THE INVENTION

It is therefore an object of the invention to disclose methods for measuring liquid flow and apparatus for practicing these methods.

It is another object of the invention to disclose a method which makes both accurate and real time measurements of relatively small flows.

It is a further object of the invention to disclose a method where optical imaging means are used for measuring the shape and change in shape of a liquid flowing through an outlet.

Another object of the invention is to disclose a method of measuring the meniscus level in a liquid.

It is a further object of the invention to disclose a method of measuring the meniscus level in a liquid collecting container to determine the back-pressure at an outlet of the container.

It is a further object of the invention to disclose a method for controlling and adjusting a flow or flow rate.

The shape of the drop is a function of mass, cohesion, adhesion and construction of the outlet, and represents a volume. This shape can result in a drop that falls from the outlet if the flow or waiting time is long enough. The change in shape in time is a direct measure of the flow. The time dependency of the change is a measure of the flow rate. This is a vital point of the method. Due to the fact that the measurement of volumes of isolated, completed, falling drops is not relevant for the invention, even the yield from a flow over a time so small that a drop will never be formed, can be measured in this way. The method can be simply implemented, requiring only known reliably produced devices.

The use of optical imaging and image processing means enables the measuring of a volume flow rate in real time with a high accuracy and results in a flexible measuring set-up to take into account other relevant parameters like environmental back-pressure. With the use of optical measurement methods, direct contact with the flowing medium is avoided.

In a preferred embodiment, the changing volume of a drop during its building-up at an outlet is measured by image acquisition and image processing. Digital, image acquisition and image processing tools are preferably used. Thereafter, image registration, processing and presentation can be quickly, accurately and clearly executed on-line. Any measurement transformation from volume into mass can be performed using the known density of the liquid. In such an embodiment, the change in shape of a drop hanging and growing at an outlet due to the liquid flow is part of the measuring method. This growth is preferably measured by processing the drop image and calculating continuously the instantaneous drop volume. From the change of shape or volume in time, the real time flow can be determined.

For optical image registration of the drop, a detector matrix like a CCD chip, a conventional video camera, an open RAM memory or other light sensitive devices is preferably used. Such a detector is arranged along the location of the growing drop. Although it may be supposed that the shape of the drop hanging at a cylindrical, vertical, outlet and under normal gravitational pull has a cylindrical symmetry, in a further preferred embodiment additional image acquisitions are taken of the growing drop in various directions. In this situation, more acquisition devices can be applied in a known manner, but also an image from different directions can be projected on the detector using optical tools, such as mirrors. In such an arrangement, corrections can be made for asymmetry and/or vibrations in the drop. Asymmetry could occur when the embodiment is not perfectly vertical. Hence the accuracy of the measuring method can be improved and the consequences of the environmental conditions minimized.

The total delivered volume of a liquid over a certain time can be calculated from a continuous integration of the flow over that time.

According to another aspect of the invention, in a preferred embodiment, the delivered volume or yield of the flow is collected in a container and the position of the meniscus in the container is measured. Knowing the diameter of that container, the increase of level in a unit of time is a measure for the flow rate as well. The change in level of the meniscus is also a measure of the change in pressure inside a container, if isolated from the outer world.

Potentially substantial evaporation which may occur during the growth of drops or level increase at very small flows can be compensated for by adapting the partial vapor pressure in the measuring container by adjusting the temperature just above the condensation point. Attention should be paid to avoid condensation on the optical parts of the measuring device, possibly by slight warming of the lenses.

In a further preferred embodiment, the container for the collected liquid has the shape of a transparent cylinder. Once filled, this cylinder acts as a cylinder lens and hence the level of the meniscus can be accurately determined due to the difference in optical properties between the filled and empty part of the container. An illumination slit is positioned, preferably parallel to the axis of the cylinder and opposite to the image acquisition device in the back focal plane of the cylinder lens formed by the filled container. In the case of an empty container, the container acts as a window and the slit will not be magnified. This changes in the case of a full container, where the slit is magnified onto the pick-up device. In another application, the light rays are bent away from the pick-up device. Such a container can be provided with an outlet from which the liquid is dosed, with or without a valve. To ensure a reproducible meniscus and to reduce the possibility of droplets at the inner wall of the container, it may be desirable to roughen the innerwalls of the container. The surface is wettened better by this treatment. Such a roughening does not hamper the measurement of the meniscus, due to the fact that the liquid in the container will smooth the surface.

In a further embodiment, the measured liquid flow rate is used to control the liquid flow in a feedback loop. The measured increase of level of the liquid in a container over a unit of time can be used to measure, control and adjust the flow rate. Determination of the increase or decrease of the content in the container can also be used for measuring the change in pressure in the container where the container is isolated from the environment.

The change in volume in the container due to the flow can be optically measured. Based on the geometrical shape of the container, the content of the volume is calculated on a continuous basis. The change of the content in the container over a unit of time is then measured, which is equal to the flow. Preferred container shapes from which the content can be measured are cylindrical measuring containers. The increase of the drop size or meniscus level in the container requires simple alterations due to the symmetry of these parameters.

In a further embodiment, measuring of a meniscus level in a liquid collecting container is used to measure the backpressure at an outlet of the container.

With such automated measuring methods as described above, a feed-back controlled and adjusted infusion pump can be assembled. Existing pumps can also be measured and checked for all the relevant parameters.

The measuring methods of the invention can be used with a wide range of dosing, measuring, controlling and regulating instruments. Two applications can be distinguished for measuring and dosing purposes. The flow rates of pumps to be checked can be determined by measuring the drops as well as the content in the container. A pump for a continuous adaptable flow can be designed using the drop measurement for feed-back of the real time yield of the flow to adjust the speed of the pump and hence the flow rate. The level of the meniscus in the measuring container is a measure of the pressure according to the gas-law, if the measuring room is isolated from the environment. Both parameters can be used for real time dosing equipment.

A method as disclosed is particularly applicable for an apparatus where an accurate determination of liquid flows or liquid flow rates is necessary, such as for example in a medical infusion apparatus.

In a preferred embodiment an apparatus according to the invention is provided with a data processing unit for checking the flow, the flow rate and the yield of a liquid dosing system upon the flow rate data obtained. Such an apparatus is particularly applicable for checking the dosing in medical treatment or diagnosis.

In a further embodiment an apparatus according to the invention is provided with a data processing unit to adjust a liquid dosing system based on flow rate data obtained. For example, such an apparatus is particularly useful to control and adjust the flow of a dosing system in a medical infusion set.

The invention will be described in more detail with reference to the drawings.

DETAILED DESCRIPTION OF THE INVENTION

Figure 1:
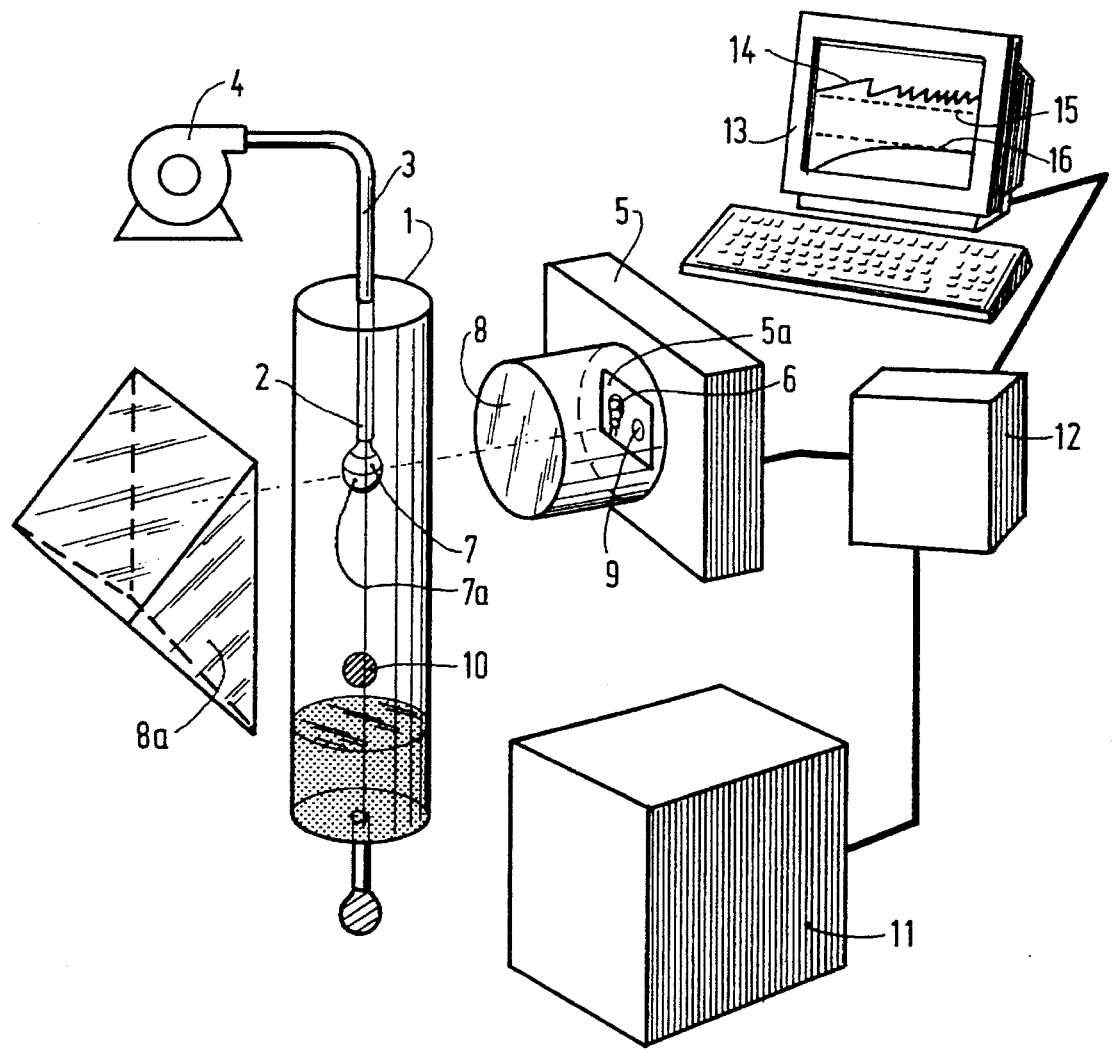
FIG. 1 shows the imaging of a growing liquid drop in accord with the invention.
Figure 2:
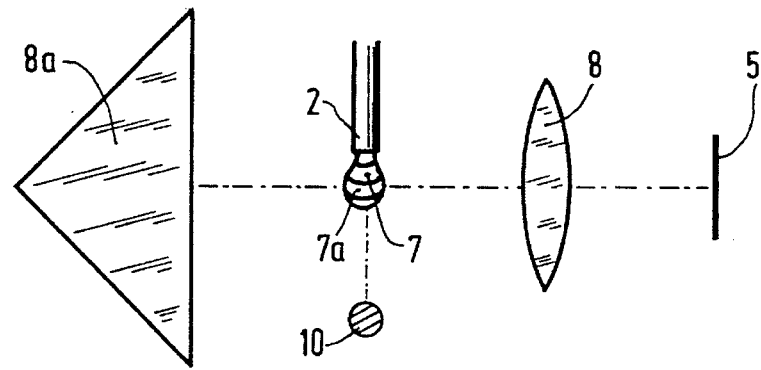
FIG. 2 shows the imaging apparatus of FIG. 1 in a system for measuring liquid flow.

A measuring system is seen in schematic form in FIGS. 1 and 2. The system includes a container 1 which supports a tubing 3 having an outlet 2, a pump 4, and an imaging device 5 with a pick-up entrance screen 5a on which an image 6 of a growing drop 7 at the outlet 2 is projected by a lens system 8. Here, a prism 8a also projects an image 9 of a falling drop 10 on the pick-up device 5. Similar set-ups 11 can be positioned at different angles with the described set-up for minimizing the influence of asymmetries. Images registered by the pick-up device 5 are processed by an image processor 12 which calculates the volume 7 of the drop and the increase of volume 7a, and represents the value or processed results on a presentation peripheral 13, e.g., a cathode ray tube (CRT). On this CRT, every growth of a drop is visible as a saw-tooth 14 in the upper graph 15. The inclination (slope) of the saw-tooth 14 is a measure of the flow rate which is presented in the lower graph 16.

Figure 3:
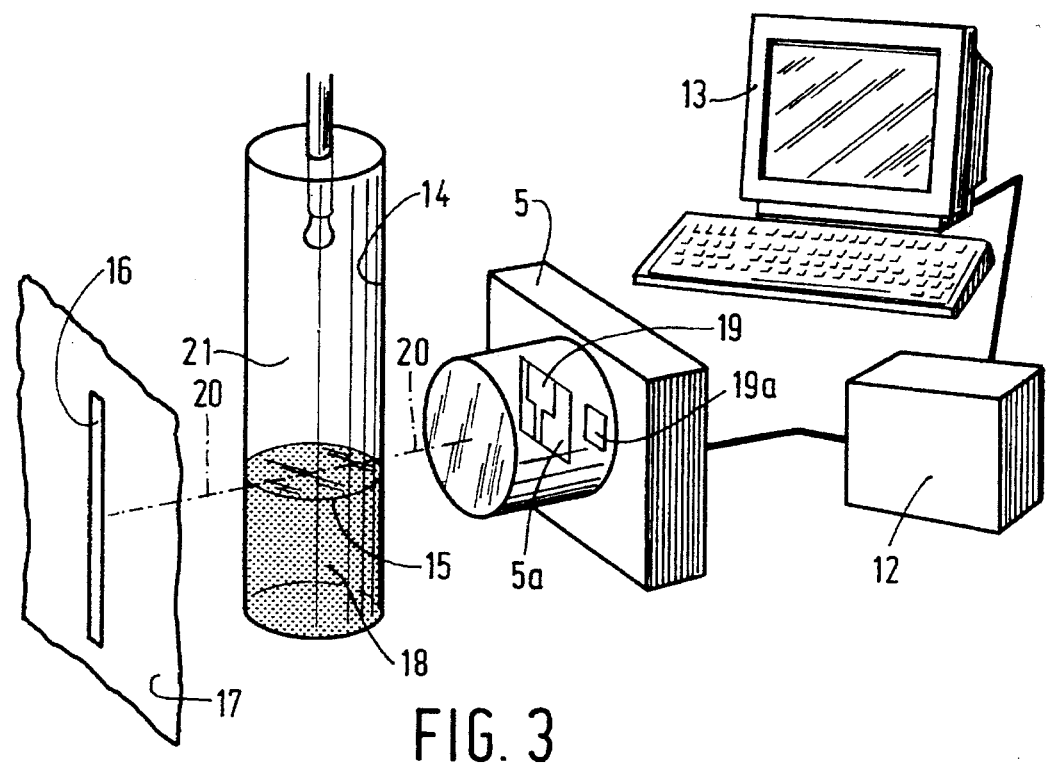
FIG. 3 shows an optical measuring system which measures the meniscus level of a liquid in a container.

A sketch of an apparatus for meniscus level detection is given in FIG. 3. In a container 114, drops or otherwise outstreaming liquid can be collected in a pool resulting in a fluid layer in the container with a meniscus 115. Opposite to an image pick-up device 5, and at the rear site of a preferably cylindrical transparant container 14, a light bar 16 is positioned in the backfocal plane 17 of the container. When the optical axes 20 of the bar, container, and pickup device 5 are aligned, the filled part 18 of the container projects a magnified image 19 on the pick-up device 5. If the optical axes 20 of the bar, container and pick-up device do not coincide, the filled part 18 of the container bends the image 19a of the bar 16 so that the image is not projected onto the entrance screen 5a. In both cases, the boundary between the image of the bar not influenced by the unfilled part 21 of the container, and the image of the bar influenced by the filled part can easily be detected by an image processor 12 which calculates the volume increase and represents the value or processed results on the CRT 13.

Figure 4:
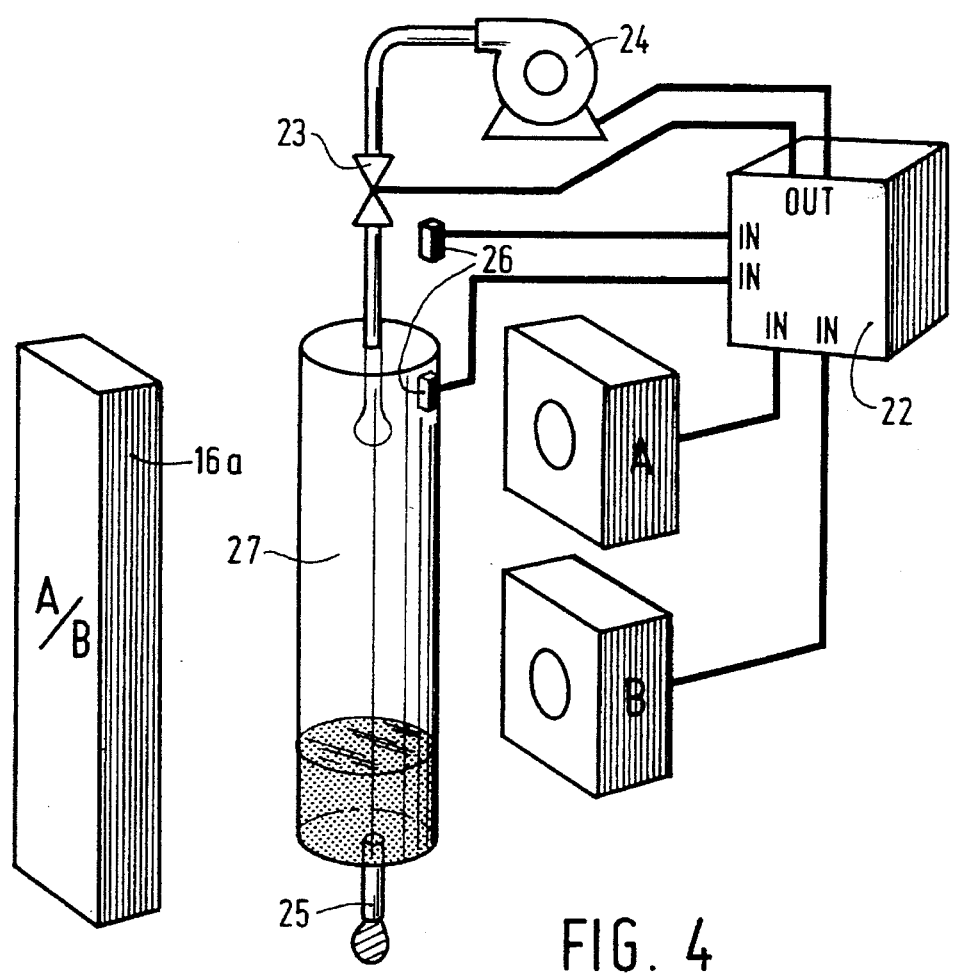
FIG. 4 shows an example of a flow-feedback regulated pump for use with the systems of FIGS. 2 or 3.

In FIG. 4, the systems of FIGS. 1–3 are combined for regulation of a flow, with an optical set-up A for drop measurement and an optical set-up B for meniscus detection. Set-up A regulates a driving force needed for meeting a required flow. An illuminating device 16a is part of set-up devices A and B. A processor unit 22 controls a valve 23 or the speed of a pump 24. Set-up B detects a meniscus level to allow compensation of a back pressure at an outlet 25 of the complete device. Pressure sensors 26 in the outer world and a drop chamber 27 can also support the control strategy due to their even faster sampling speed. A combination of set-up A and set-up B presents the principles of a general dosing system which can be profitably applied for example in infusion systems for medical use. Due to the technique of drip chambers, which have already been in use for a long time in hospitals, the method is easily acceptable.

I claim:

1. A method for measuring the flow rate of a liquid flowing as droplets through an outlet, comprising:

a) using optical imaging means, measuring the shape of a droplet of the liquid at the outlet at first and second instants in time, said first and second instants in time providing a time interval; and b) using processing means, determining a first volume of said droplet at said outlet at said first instant in time based on the shape of the droplet at said first instant in time, and determining a second volume of said droplet at said outlet at said second instant in time based on the shape of the droplet at said second instant in time, and taking a difference between said second and first volumes to determine a volume growth for said time interval, said volume growth for said time interval defining the flow rate of the liquid.

2. A method according to claim 1, further comprising:

monitoring the volume of said droplet at the outlet over additional instances in time, wherein a determined change in volume over a determined period of time defines the flow rate for that determined period of time.

3. A method according to claim 2, further comprising:

using the flow rate in a feedback manner, controlling the flow rate of the liquid.

4. A method according to claim 2, further comprising:

repeating steps a) and b) for a plurality of different droplets over a long period of time relative to said time interval to provide said flow rate.

5. A method according to claim 1, wherein:

the volume of the said droplet is measured using image acquisition and image processing means.

6. A method according to claim 5, wherein:

the volume of the said droplet is measured using a plurality of image acquisition means located at different orientations relative to said droplet.

7. A method according to claim 1, wherein:

the liquid is collected in a container and forms a meniscus, and the method further comprises measuring the level of the meniscus in the container at different points in time, and determining a flow rate of the liquid as a function of a change of the level of the meniscus over time.

8. A method according to claim 7, wherein the container has a container outlet, further comprising:

using said height meniscus level to measure a backpressure at the container outlet.

9. A method according to claim 1, further comprising:

integrating volume differences over a period of time to provide said flow rate.

10. A method according to claim 1, wherein:

said shape of said droplet is measured by said optical imaging means by acquiring information from a plurality of different directions.

11. An apparatus for measuring either a flow rate of a liquid, comprising:

a) a fluid outlet through which the liquid flows and forms a droplet;

b) an imaging means for imaging said droplet at different instants in time;

c) projection means for projecting images of said droplet onto said imaging means; and d) processing means coupled to said imaging means for determining the different volumes of said droplet at different instants in time from the images of said droplet projected onto said imaging means, for taking the difference between said different volumes to provide a volume growth of said droplet, and for determining said flow rate based on said volume growth of said droplet over a period of time defined by said different instants.

12. An apparatus according to claim 11, wherein:

said imaging means for imaging said droplet comprises a plurality of imaging apparatus which image said droplet from a plurality of different directions, and said projection means for projecting an image of said droplet onto said imaging means comprises a plurality of projection apparatus which project respective images of said droplet onto respective of said imaging apparatus.

13. An apparatus according to claim 11, wherein:

said processing means includes integration means for integrating volume differences over a period of time to provide said flow rate.

14. An apparatus according to claim 11, further comprising:

means coupled to said processing means for adjusting the flow rate of the liquid based on said flow rate as determined by said processing means.

15. An apparatus according to claim 11, wherein:

said imaging means comprises a lens means having a pickup entrance screen.

16. An apparatus according to claim 15, wherein:

said imaging means further comprises a prism located opposite said lens means.

* * * * *